United States Patent [19]
Christie et al.

[11] Patent Number: 5,112,351
[45] Date of Patent: May 12, 1992

[54] MULTIFOCAL INTRAOCULAR LENSES

[75] Inventors: Bruce Christie; Amitava Gupta, both of Irwindale, Calif.

[73] Assignee: Ioptex Research Inc., Irwindale, Calif.

[21] Appl. No.: 596,681

[22] Filed: Oct. 12, 1990

[51] Int. Cl.$^5$ .......................... A61F 2/16; G02C 7/04; G02C 7/06
[52] U.S. Cl. ...................................... 623/6; 351/161; 351/168; 351/169
[58] Field of Search ..................... 623/6; 351/161, 168, 351/169

[56] References Cited

U.S. PATENT DOCUMENTS

| 4,769,033 | 9/1988 | Nordan | 623/6 |
| 4,830,481 | 5/1989 | Futhey et al. | 351/161 |
| 4,898,461 | 2/1990 | Portney | 351/161 X |
| 4,917,681 | 4/1990 | Nordan | 623/6 |

FOREIGN PATENT DOCUMENTS

WO90/00889 2/1990 PCT Int'l Appl. .................... 623/6

OTHER PUBLICATIONS

Article Published in Journal of Cataract and Refractive Surgery Jan. 1988 (pp. 17-24), author Jack T. Holladay, M.D.

*Primary Examiner*—Ronald Frinks
*Attorney, Agent, or Firm*—Rosenman & Colin

[57] ABSTRACT

A multifocal intraocular lens is produced which comprises a lens body having a plurality of optical zones which comprises an aspheric optical zone between each add and base power zone thereby providing a gradual transition in the curvature of the optic surface and avoiding abrupt changes in the curvature of the optic.

12 Claims, 7 Drawing Sheets

MULTIFOCAL INTRAOCULAR LENSES

THE PRESENT INVENTION

The present invention is concerned with multifocal intraocular lenses (IOLs) which comprise a lens body having a multiplicity of optical zones wherein an aspheric optical zone is interspersed between add and base power zones.

Bifocal and multifocal intraocular lenses are known in the art and some are currently undergoing clinical trials. While multifocal IOLs are expected to provide good visual acuity for at least two focal points and also greater depth of vision than monofocal IOLs, multifocal IOLs cannot be expected to match the optical performance of monofocal IOLs in terms of image strength and image quality at a given focus. This is because the percent light intensity illuminating the best focused image will be lower for a multifocal IOL relative to monofocal IOL, and the image contrast will thus suffer because of the presence of an unfocused second image While the human visual system is very tolerant of brightness variations, and can extract a great deal of information from low contrast images by virtue of the image processing that occurs in the retina and visual centers of the brain, studies of dependance of visual acuity on illumination levels show that a 100 fold change in illumination causes a 50% decrease in visual acuity at moderate illumination levels while the rate of change in visual acuity is much smaller at very low and very high illumination levels. Thus, the quality of vision which a patient will experience is not solely dependent on the image strength and contrast but is also dependent on the totality of usable visual information presented at the macula.

In U.S. Pat. No. 4,636,211, Nielsen describes a bifocal optic with concentric optical zones of a base power needed for emmetropia or distance vision and an add power designed to provide vision at near or intermediate distances. According to this design, the central portion of the optic constitutes the zone with the add power while the periphery constitutes the zone with the base power. Such an IOL optic may not be suitable for patients with pupil sizes smaller than 2 mm. Kalb has attempted to solve this problem by developing a three zone bifocal lens which provides a central zone for distance vision surrounded by an annular zone embodying the add power for near vision, and the periphery for distance vision. This design tends to minimize the potential loss of distance vision in patients but does not take into account variations in pupil size which occur at varying light levels. Thus, the location and sizes of the various power optic zones have heretofore not been optimized for changes in pupillary diameters which occur as a result of variations in the ambient light levels, nor have the visual tasks which one may expect to perform under various light levels been taken into account in designing IOLs according to the prior art.

Since the area of the optic zone of a given focal length included in the pupillary aperture is proportional to the image strength produced at that focus, visual acuity achieved by a patient who receives an intraocular bifocal optic would be expected to be dependent upon the area of the optic zones at the base and add powers seen through the pupillary aperture. The Kalb design does not optimize for the balance of image strength at different pupil diameters and multifocal optical designs based on diffraction theory do not allow any variation of image strength for near and distance objects as pupillary diameters change. Since the variation of illumination levels is usually smaller indoors than outdoors, variation of pupillary sizes is also smaller indoors than outdoors. Light levels are therefore expected to be at intermediate levels indoors while outdoor light intensity may reach a high level when there is bright sunlight or it may be at a very low level on moonless nights. Since indoor visual tasks mostly require intermediate and near vision, the design of a multifocal IOL should provide the strongest image intensity for near objects at intermediate pupillary sizes. Similarly, outdoor visual tasks usually require distance vision and hence the IOL should be optimized to provide the strongest possible image intensity for distant objects at the extreme values of pupillary sizes. Heretofore no one has taken these factors into consideration in designing multifocal intraocular lenses.

The designs discussed above are bifocal in nature and thus they utilize optic zones of two different focal lengths only. One of these zones is selected to achieve emmetropia of distance while the other provides an add power typically of 2.5 to 4.5 diopter which corresponds to a reading distance of about 11 to 20 inches. This design of lens fails to provide any image intensity for objects at an intermediate distance which requires the use of intermediate power zones or aspheric optics.

According to the present invention it has been discovered that when aspheric optical zones are interspersed between add and base power zones, one obtains a gradual transition in the curvature of the optic surface and avoids abrupt changes in the curvature of the optic. The resulting optic is smooth and lacks transition lines which cause scattering of light leading to the patient's sensation of glare or ghost images. Aspheric zones contribute additional image intensity at both distant and near foci.

The use of aspheric zones in intraocular optics was first described in U.S. Pat. No. 4,769,033 by Dr. Nordan. However, the designs disclosed by Dr. Nordan were not centrosymmentric and were not optimized either for pupillary size or for illumination level variations, nor did they suggest the aspheric zone be placed between the add and base power zones.

More particularly, the present invention is concerned with a multifocal intraocular lens which comprises a lens body having at least five optical zones wherein aspheric optical zones are interspersed between add and base power zones.

According to one embodiment of the present invention a multifocal intraocular lens is produced which comprises a lens body having a plurality of optical zones which comprises add power zones and base power zones and an aspheric optical zone disposed between each add and base power zones thereby providing a gradual transition in the curvature of the optic surface and avoiding abrupt changes in the curvature of the optic.

According to a further embodiment of the present invention a multifocal intraocular lens is produced which comprises a lens body having at least five optical zones, a first zone comprising a central constant power zone for distance vision, a second zone comprising an annular aspheric zone, a third zone comprising a constant power zone for near vision, a fourth zone comprising an aspheric zone to bring the power back to the distance vision level and a fifth zone comprising a constant power zone for distance vision, whereby the radii for each optical zone is determined to minimize aspherical aberrations and wherein the percent optical area for near and distance vision is calculated based on pupillary diameter and variation of pupillary apertures in humans for whom said lenses are designed.

According to a further embodiment the multifocal intraocular lens is centrosymmentric.

Preferably the multifocal intraocular lens according to the present invention has five zones.

The multifocal intraocular lenses according to the present invention may have two loops secured to the lens body or optic, wherein loops are preferably substantially symmetrically disposed.

Alternatively, the multifocal intraocular lens may have two loops integral with the lens body wherein the loops are substantially symmetrically disposed.

The multifocal intraocular lenses of the present invention are constructed so that a human having such a lens implanted in his eye perceives objects at an intermediate distance through 5 to 13 percent of the overall image intensity thereby enhancing the depth of field perception, objects at a near distance through 18 to 58 percent image intensity and objects at a distance through 35 to 78 percent of the image intensity.

The present invention also includes a method of providing vision to a human who has had his natural lens removed which comprises implanting in the eye of the human indeed thereof a multifocal intraocular lens according to the present invention.

In designing the multifocal IOLs according to the present invention, I have computed the optimum size and location of the various optical zones in order to achieve the best combination of image intensities as a function of pupillary diameter and illumination levels.

The present invention may be more readily appreciated by reference to the drawings wherein:

FIG. 1A shows a multifocal IOL according to the present invention which comprises five zones:

1 is a central constant power zone designed for distance vision and preferably has a radius of 0.75 mm. 2 is an annular aspheric zone, designed to provide from 0 to 3D add, extending to a radius of about 0.95 mm. 3 is a constant power zone which incorporates a constant 3D add, and is designed for near vision and extends to a radius of about 1.3 mm. 4 is an aspheric zone, designed to bring the power back to the distance visual level and extends to a radius of about 1.5 mm. 5 is a constant power zone designed for distance vision and extends to the lens periphery. 6 represents two typical loops or haptics which may be secured to the optic by techniques per se known or alternatively which may be integral with the lens to form a 1-piece multifocal IOL.

Image strengths at distant and near foci for variation of pupillary apertures and illumination levels were used to derive the zonal locations and areas. I have found it convenient to use a computer program to optimize the image strengths. FIG. 3 shows plots of per cent optical area available for distance and near foci for three arbitrary centrosymmentric multifocal optic designs using the same computer program.

Figure 3A:
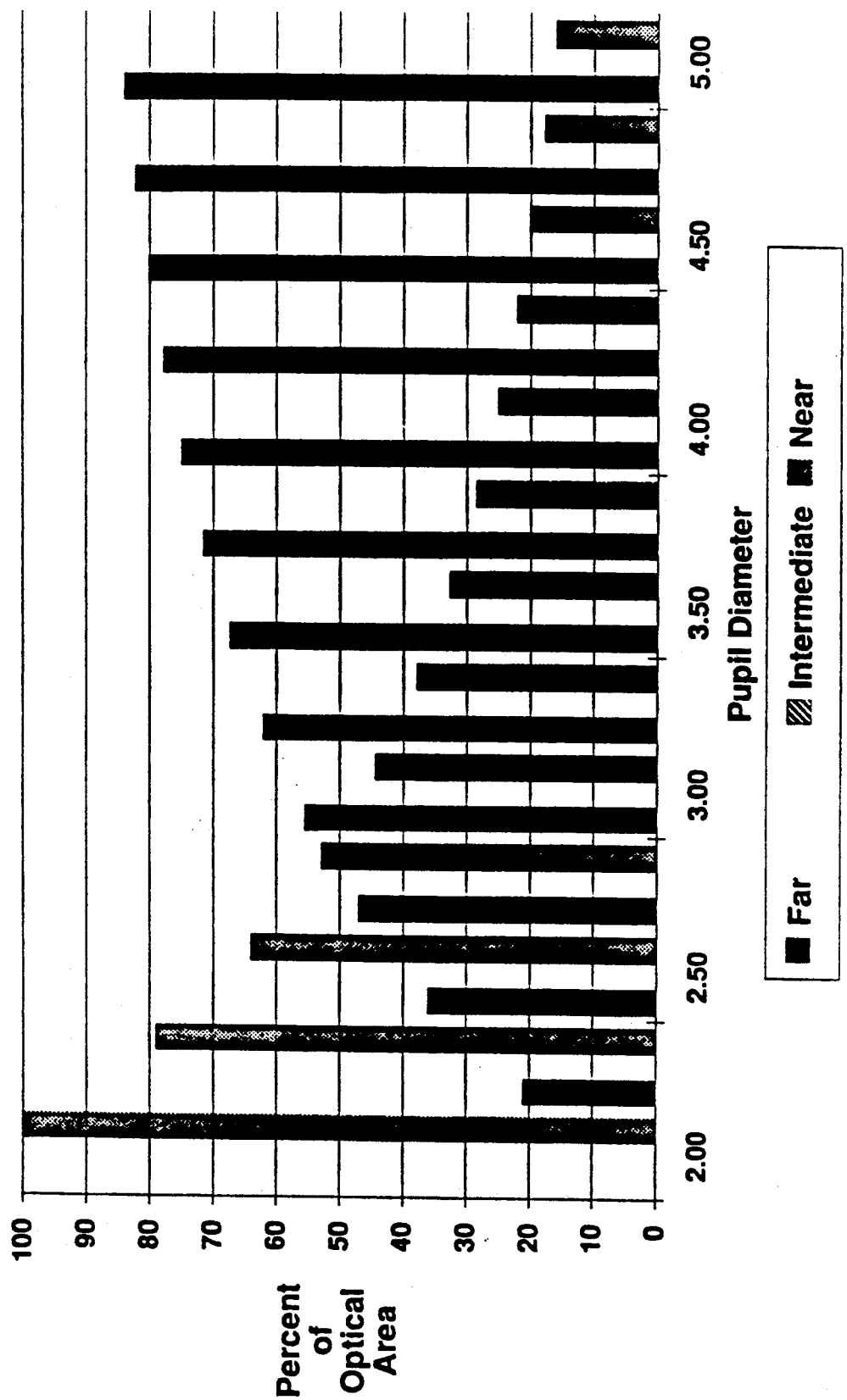
Figure 3B:
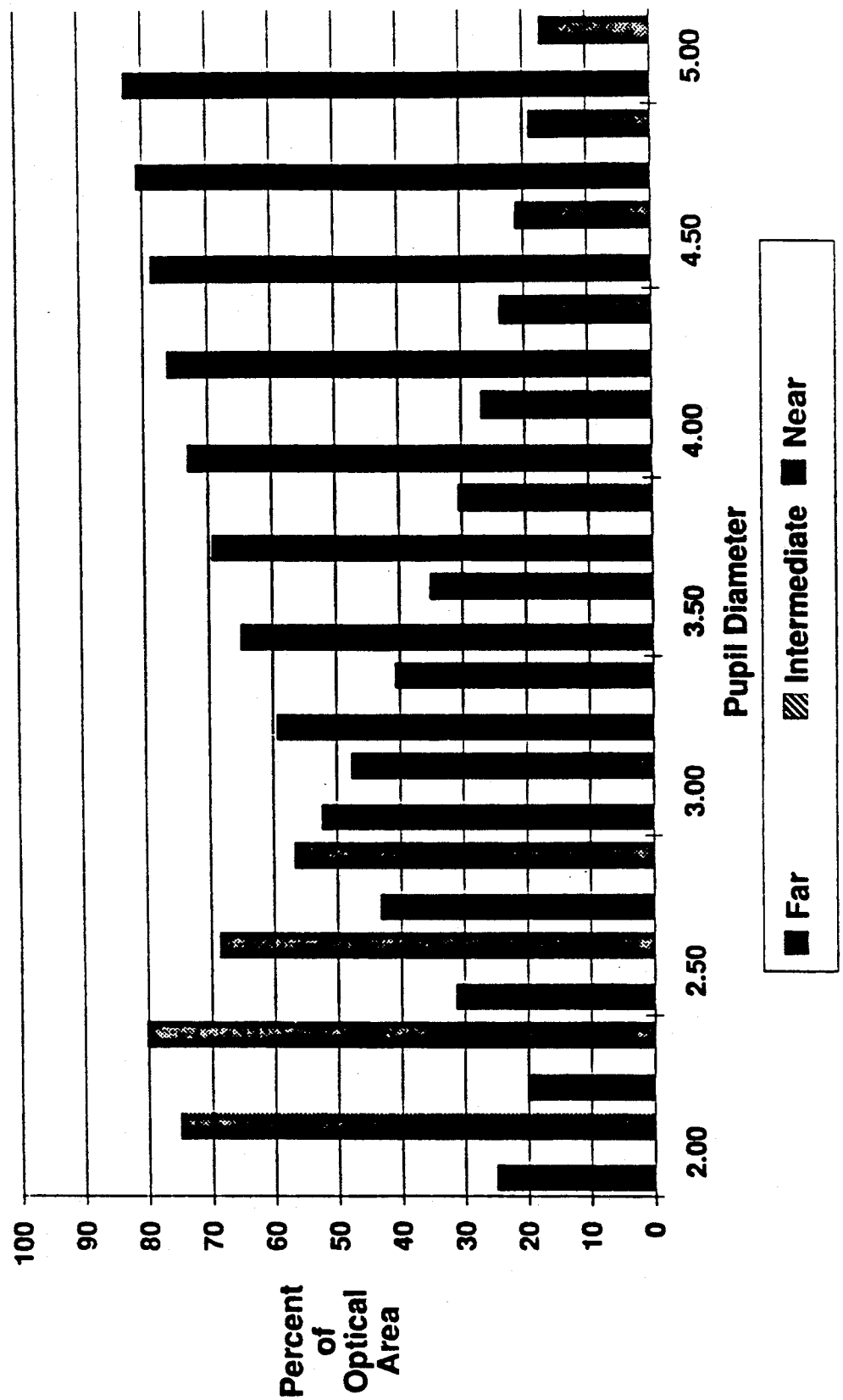
Figure 3C:
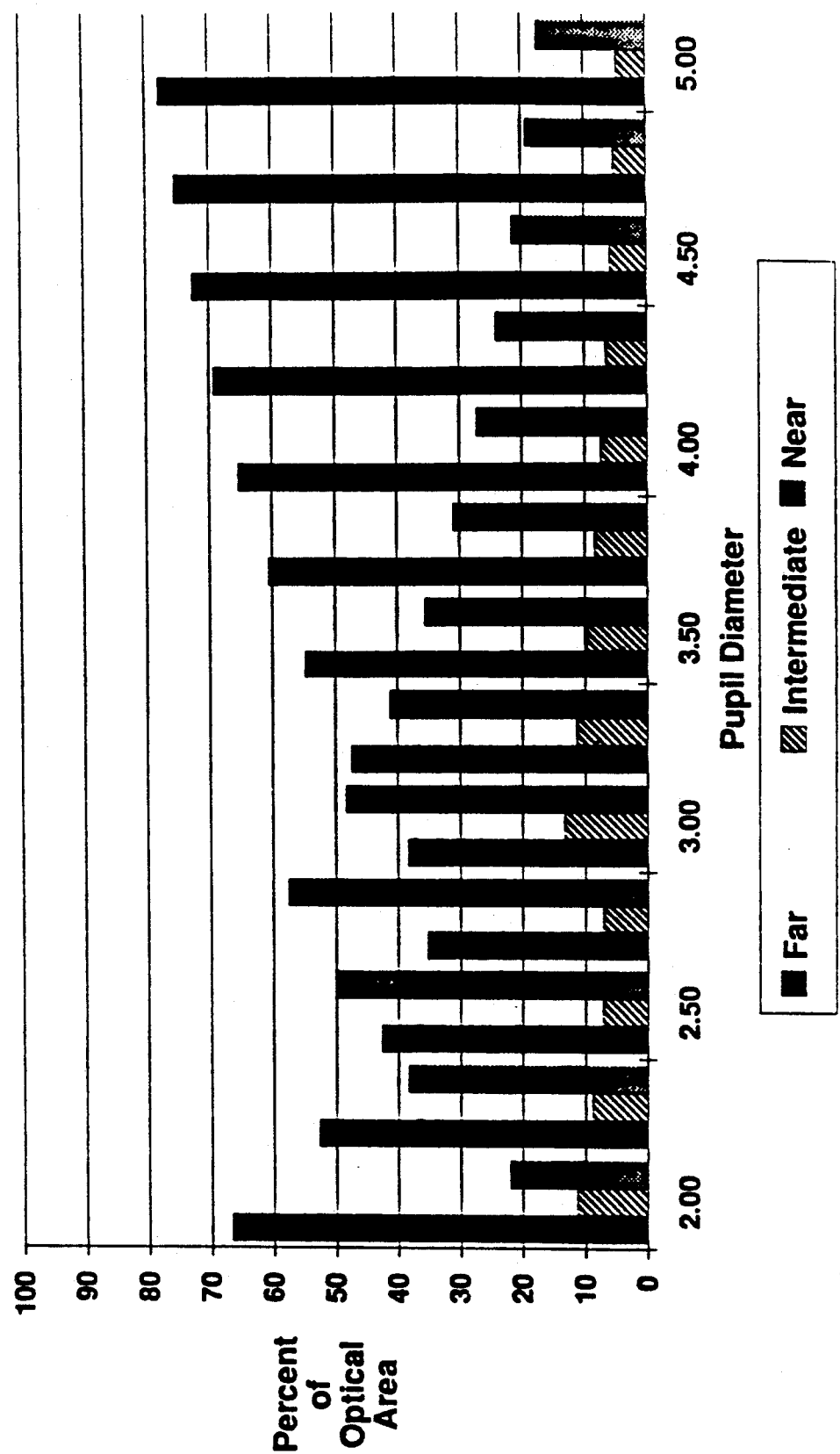

FIG. 3a shows a two-zone bifocal lens with a 2 mm diameter central add and peripheral distance zone. FIG. 3b shows a three-zone bifocal lens with a 1 mm diameter central distance, 2.30 mm diameter annular add and peripheral distance zones. FIG. 3c shows a five zone multifocal IOL according to the present invention.

If one assumes that the percent optical area available for each focus is linearly proportional to the image intensity at that focus, then these plots give one measure of optical performance of each of the designs Using this approach to estimate image intensity for each focus, I selected a design which provides a preponderance of image strength at the distance focus for small and large pupillary diameters while giving emphasis to the image strength at the near focus for intermediate pupillary diameters. This was based on my belief that while the light level outdoors may be either very high or very low causing the pupil to contract or dilate to its extreme sizes, indoor lighting generally will be at intermediate levels resulting in intermediate pupillary apertures. Exceptions may exist such as when one reads under a bright light which shines directly in a patient's face or perhaps at dusk or twilight illumination which might produce a level of illumination below that generally experienced outdoors.

Figure 1A:
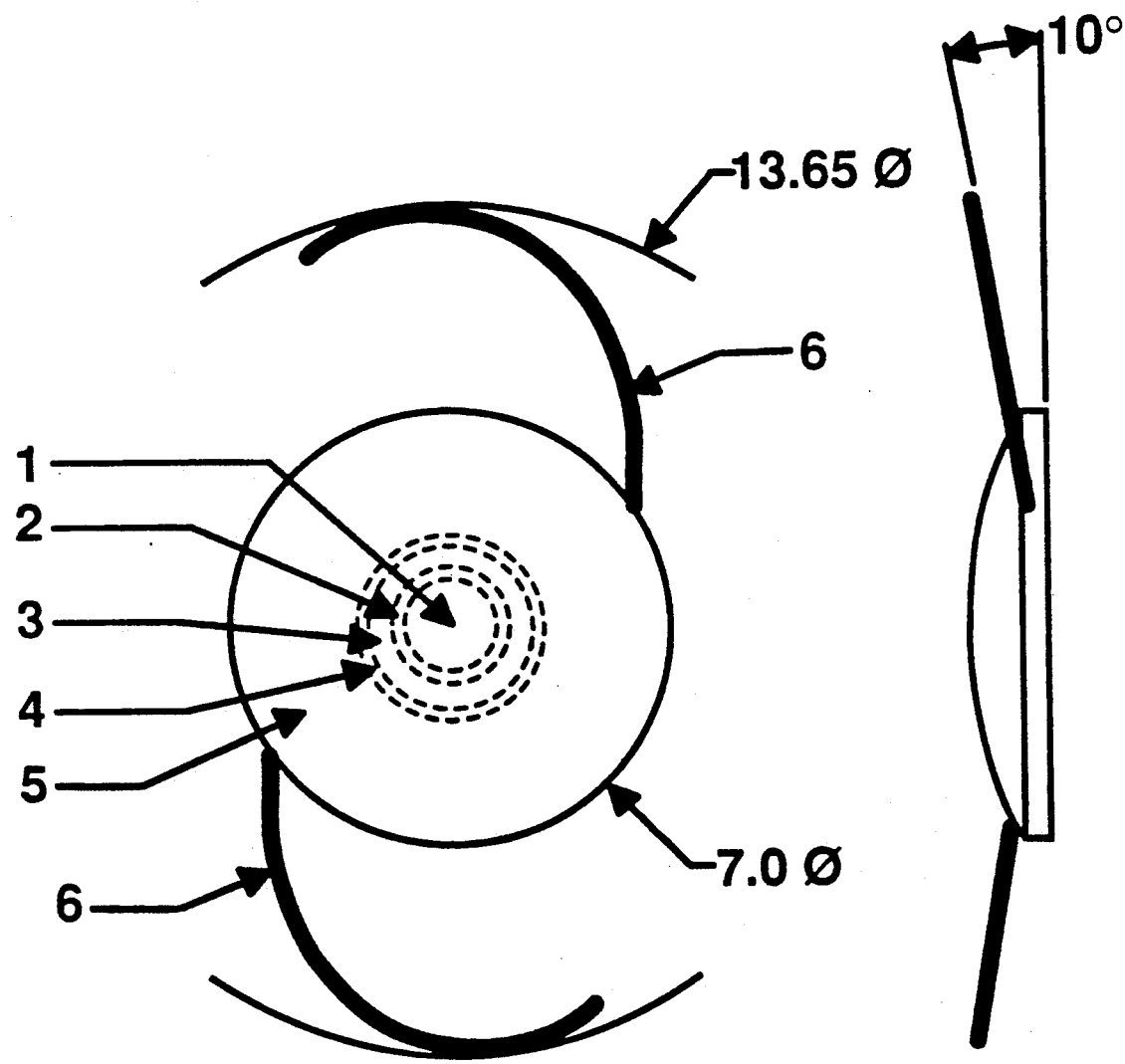
FIG. 1b shows a plot of variation of lens power with distance from the center of the optic. The radii of the optical zones were determined by a computer program which computed per cent optical area contributing to near and distance image intensities as a function of pupillary diameter.
Figure 1B:
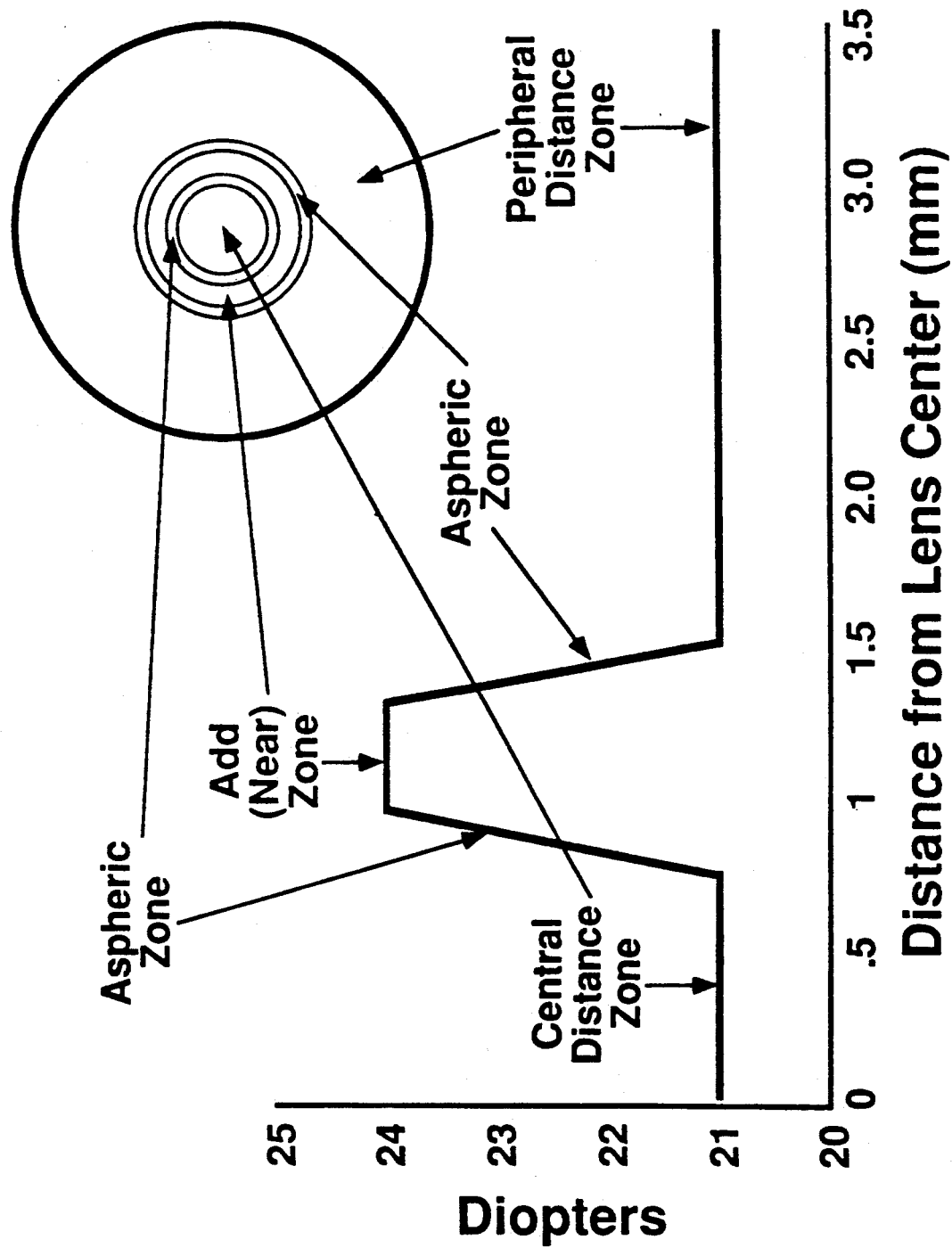
Figure 2A:
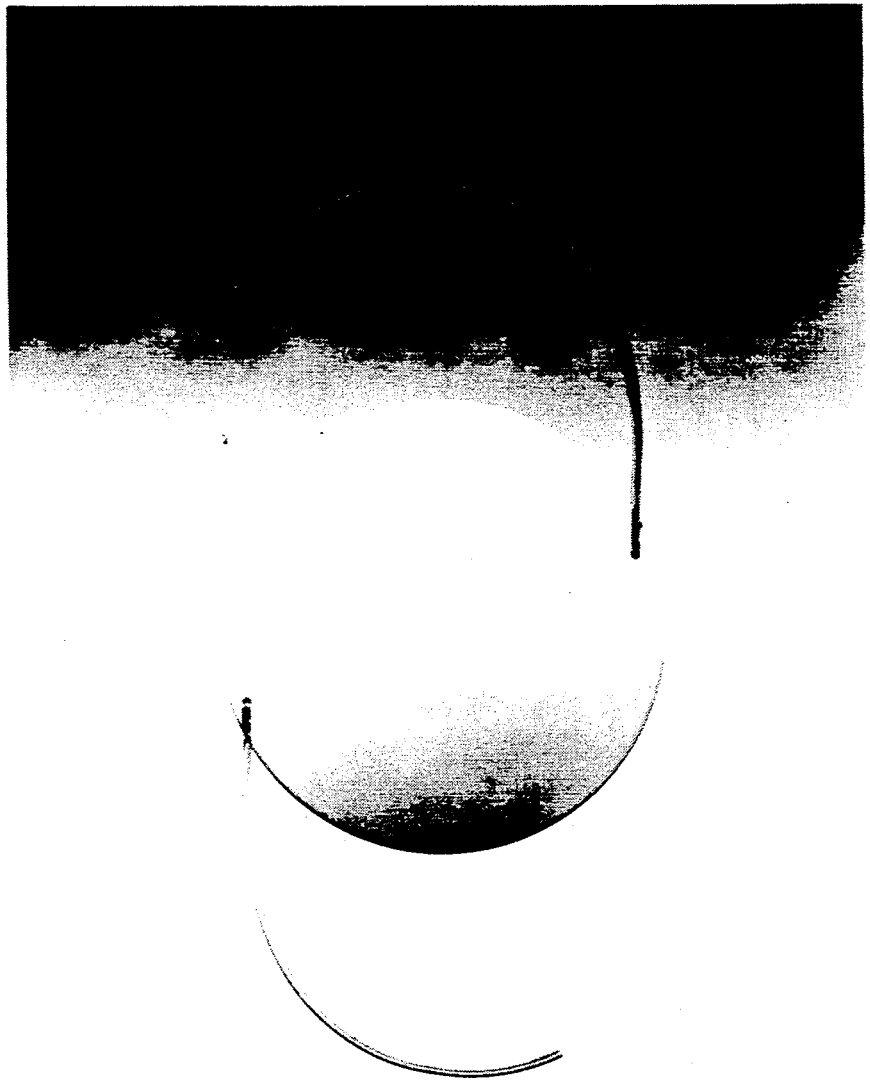
FIGS. 2a and 2b show the surface quality of the optic as examined by optical and scanning electron microscopy (SEM). The surface geometry of the multifocal IOLs according to the present invention was designed to minimize spherical aberrations and I have found that machining on an air bearing lathe is beneficial.
Figure 2B:
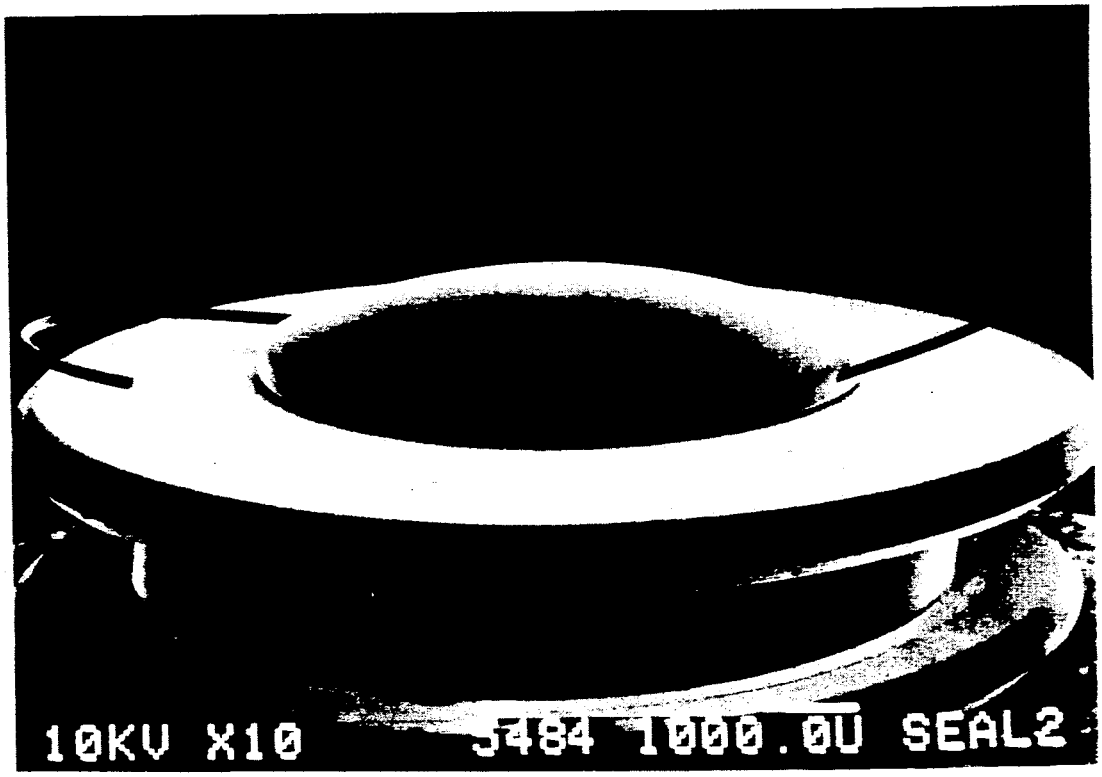

Since distance vision is most typically needed outdoors and near vision is most typically needed indoors, I have selected the design shown in FIG. 1b to address these needs FIG. 3c shows the image intensity distribution for the multifocal IOL according to the present invention. Objects at intermediate distances typically receive 5–13% of the overall image intensity, thereby enhancing the depth of field, while 18–58% of the image intensity is received at near distances and 35–78% of the image intensity is received for distance objects. The presence of the aspheric zones according to the present invention provide three distinct benefits. First, they allow the curvature of the optic surface to vary continuously (see FIGS. 2a and 2b; which eliminate any abrupt changes in surface slope which would be visible as lines on the optic surface of bifocal IOLs.) FIGS. 2a and 2b clearly demonstrate that the surface of an aspheric multifocal IOL does not contain any discrete lines which function as scattering entities and cause glare and discomfort to the wearer. Secondly, the aspheric portions directly adjacent to the near and distance focusing zones contribute to the image intensities at those two foci and enhance the near and distance focal imaging performance of the lens (it is estimated that up to $\frac{1}{3}$ of the aspheric adjacent to the distance and near focusing zones contribute in this manner). Thirdly, the aspheric portions actually produce usable image intensity at intermediate distances as shown by a through focus MTF analysis performed at 3 mm and 5 mm pupillary apertures. Measurements of MTF at focal distances between the two foci were performed and compared with MTF measurements of a monofocal lens at similar defocus. In each case, the image quality at intermediate distances was found to be significantly higher than a monofocal optic of same size and power. The following non-limitative Example more particularly illustrates the patent invention.

EXAMPLE

The centrosymmentric design incorporating aberration corrected spherical and aspheric zones was produced on a diamond turning machine. The first step is to determine the magnitude of the add power which will impart the best visual acuity at near distances. Table 1 provides results of a calculation based on the Holladay model of the human eye *Journal of Cataract and Refractive Surgergy*, Jan. 1988, pages 17-24. From this table one finds that an add power of 3.0D will provide a reading distance of 17 inches. For all patients, add powers ranging from 2.5 D to 4.5 D is desired, while the preferred range is 3.0 D-4.0 D.

The IOL optic is manufactured by conventional lathe cutting methods, starting from plastic discs 10-12 mm in diameter, and 2-4 mm in thickness. These discs are lapped on one side, then mounted on a tool using an adhesive tape or semi soft wax. The tool is then inserted into the collet of the radius turning machine. A software package is used for control of the movement of the part and the tool utilizes a precalculated set of point coordinates describing the entire optic curve. An illustrative set of print coordinates is set forth in Table 2. After the optic curve has ben cut, holes are drilled in the side of the optics for placement of haptics. The part is detached from the holding tool, and loops or haptics made of polypropylene or other polymers are then inserted into the radial holes. Haptics are entrapped in place by conventional techniques. The complete IOL is then polished by tumbling in glass jars containing a suspension of fine aluminium oxide polish in water and glass beads. The polished IOL packaged and sterilized or may undergo further surface treatment prior to being packaged.

TABLE 1

Reading Distance vs. Add Power

| Add Power (D) | Add Difference (ΔD) | Expected Ref. (D) | Reading Dist. (in) |
|---|---|---|---|
| 18.50 | 0.00 | 0.00 | infinity |
| 18.75 | 0.25 | −0.18 | 218.72 |
| 19.00 | 0.50 | −0.37 | 106.41 |
| 19.25 | 0.75 | −0.56 | 70.30 |
| 19.50 | 1.00 | −0.75 | 52.49 |
| 19.75 | 1.25 | −0.94 | 41.88 |
| 20.00 | 1.50 | −1.14 | 34.54 |
| 20.25 | 1.75 | −1.33 | 29.60 |
| 20.50 | 2.00 | −1.52 | 25.90 |
| 20.75 | 2.25 | −1.72 | 22.89 |
| 21.00 | 2.50 | −1.92 | 20.51 |
| 21.25 | 2.75 | −2.12 | 18.57 |
| 21.50 | 3.00 | −2.32 | 16.97 |
| 21.75 | 3.25 | −2.52 | 15.62 |
| 22.00 | 3.50 | −2.72 | 14.47 |
| 22.25 | 3.75 | −2.92 | 13.48 |
| 22.50 | 4.00 | −3.13 | 12.58 |
| 22.75 | 4.25 | −3.33 | 11.82 |
| 23.00 | 4.50 | −3.54 | 11.12 |
| 23.25 | 4.75 | −3.75 | 10.50 |
| 23.50 | 5.00 | −3.96 | 9.94 |

Base power of 18.5 diopters will achieve emmetropia in the average U.S. patient (43.81 D K, 23.5 mm AL). Expected refractions have been computed with the Holladay formula, S Factor = .431 (A Constant = 116.6).

TABLE OF COORDINATES  TABLE 2

MULTIFOCAL SAG TABLE FOR A 21 BASE AND 24 ADD POWERS

| | |
|---|---|
| 0.0000000000 | 0.1137536994E-02 |
| 0.1682692380E-05 | 0.1226725715E-02 |
| 0.6730770490E-05 | 0.1319280530E-02 |
| 0.1514423725E-04 | 0.1415201490E-02 |
| 0.2692309750E-04 | 0.1514488653E-02 |
| 0.4206735807E-04 | 0.1617142076E-02 |
| 0.6057702768E-04 | 0.1723161816E-02 |
| 0.8245211703E-04 | 0.1832547937E-02 |
| 0.1076926387E-03 | 0.1945300501E-02 |
| 0.1362986074E-03 | 0.2061419572E-02 |
| 0.1682700395E-03 | 0.2180905219E-02 |
| 0.2036069535E-03 | 0.2303757510E-02 |
| 0.2423093699E-03 | 0.2429976517E-02 |
| 0.2843773109E-03 | 0.2559562311E-02 |
| 0.3298108009E-03 | 0.2692514968E-02 |
| 0.3786098660E-03 | 0.2828834565E-02 |
| 0.4307745346E-03 | 0.2968521181E-02 |
| 0.4863048366E-03 | 0.3111574895E-02 |
| 0.5452008042E-03 | 0.3257995792E-02 |
| 0.6074624713E-03 | 0.3407783954E-02 |
| 0.6730898740E-03 | 0.3560939470E-02 |
| 0.7420830500E-03 | 0.3717462427E-02 |
| 0.8144420393E-03 | 0.3877352916E-02 |
| 0.8901668837E-03 | 0.4040611029E-02 |
| 0.9692576268E-03 | 0.4207236860E-02 |
| 0.1051714314E-02 | 0.4377230506E-02 |

| | |
|---|---|
| 3.4553592366E-32 | 0.1963794740E-01 |
| 0.4727321638E-02 | 0.2000350583E-01 |
| 0.4907419326E-02 | 0.2037244121E-01 |
| 0.5090885233E-02 | 0.2074475376E-01 |
| 0.5277719465E-02 | 0.2112044369E-01 |
| 0.5467922131E-02 | 0.2149951122E-01 |
| 0.5661493340E-02 | 0.2188195658E-01 |
| 0.5858433204E-02 | 0.2226777997E-01 |
| 0.6058741837E-02 | 0.2265698163E-01 |
| 0.6262419355E-02 | 0.2304956178E-01 |
| 0.6469465875E-02 | 0.2344552064E-01 |
| 0.6679881517E-02 | 0.2384485846E-01 |
| 0.6893666403E-02 | 0.2424757545E-01 |
| 0.7110820656E-02 | 0.2465367186E-01 |
| 0.7331344402E-02 | 0.2506314791E-01 |
| 0.7555237768E-02 | 0.2547600385E-01 |
| 0.7782500884E-02 | 0.2589223991E-01 |
| 0.8013133881E-02 | 0.2631185634E-01 |
| 0.8247136893E-02 | 0.2673485338E-01 |
| 0.8484510054E-02 | 0.2716123127E-01 |
| 0.8725253502E-02 | 0.2759099027E-01 |
| 0.8969367376E-02 | 0.2802413061E-01 |
| 0.9216851817E-02 | 0.2846065256E-01 |
| 0.9467706969E-02 | 0.2890055636E-01 |
| 0.9721932976E-02 | 0.2934384227E-01 |
| 0.9979529986E-02 | 0.2979051055E-01 |
| 0.1024049815E-01 | 0.3024056146E-01 |
| 0.1050483761E-01 | 0.3069399526E-01 |
| 0.1077254853E-01 | 0.3115081220E-01 |
| 0.1104363106E-01 | 0.3161101256E-01 |
| 0.1131808535E-01 | 0.3207459661E-01 |
| 0.1159591158E-01 | 0.3254156461E-01 |
| 0.1187710988E-01 | 0.3301191683E-01 |
| 0.1216168044E-01 | 0.3348565354E-01 |
| 0.1244962341E-01 | 0.3396277503E-01 |
| 0.1274093896E-01 | 0.3444328156E-01 |
| 0.1303562726E-01 | 0.3492717343E-01 |
| 0.1333368848E-01 | 0.3541445090E-01 |
| 0.1363512279E-01 | 0.3590511426E-01 |
| 0.1393993036E-01 | 0.3639916380E-01 |
| 0.1424811138E-01 | 0.3689659980E-01 |
| 0.1455966602E-01 | 0.3739742255E-01 |
| 0.1487459446E-01 | 0.3790163235E-01 |
| 0.1519289689E-01 | 0.3841079477E-01 |
| 0.1551457348E-01 | 0.3892492318E-01 |
| 0.1583962442E-01 | 0.3944405776E-01 |
| 0.1616804991E-01 | 0.3996822956E-01 |
| 0.1649985013E-01 | 0.4049747047E-01 |
| 0.1683502528E-01 | 0.4103181255E-01 |
| 0.1717357554E-01 | 0.4157128818E-01 |
| 0.1751550111E-01 | 0.4211593005E-01 |
| 0.1786080220E-01 | 0.4266577117E-01 |
| 0.1820947900E-01 | 0.4322394487E-01 |
| 0.1856153172E-01 | 0.4378118482E-01 |
| 0.1891696055E-01 | 0.4434682499E-01 |
| 0.1927576571E-01 | 0.4491779971E-01 |

| | |
|---|---|
| 0.4549414366E-01 | 0.8625795863E-01 |
| 0.4607589182E-01 | 0.8711095870E-01 |
| 0.4666307958E-01 | 0.8796787533E-01 |
| 0.4725574262E-01 | 0.8882870918E-01 |
| 0.4785391704E-01 | 0.8969346090E-01 |
| 0.4845763925E-01 | 0.9056213117E-01 |
| 0.4906694606E-01 | 0.9143472065E-01 |
| 0.4968187464E-01 | 0.9231123001E-01 |
| 0.5030246256E-01 | 0.9319165993E-01 |
| 0.5092874775E-01 | 0.9407601108E-01 |
| 0.5156076852E-01 | 0.9496428415E-01 |
| 0.5219856362E-01 | 0.9585647982E-01 |
| 0.5284217215E-01 | 0.9675259878E-01 |
| 0.5349163364E-01 | 0.9765264172E-01 |
| 0.5414698803E-01 | 0.9855660932E-01 |
| 0.5480827568E-01 | 0.9946450229E-01 |
| 0.5547553737E-01 | 0.1003763213 |
| 0.5614881430E-01 | 0.1012920671 |
| 0.5682814811E-01 | 0.1022117404 |
| 0.5751358089E-01 | 0.1031353419 |
| 0.5820515518E-01 | 0.1040628722 |
| 0.5890291394E-01 | 0.1049943322 |
| 0.5960690065E-01 | 0.1059297225 |
| 0.6031715919E-01 | 0.1068690439 |
| 0.6103373397E-01 | 0.1078122970 |
| 0.6175666986E-01 | 0.1087594826 |
| 0.6248601220E-01 | 0.1097106015 |
| 0.6322180687E-01 | 0.1106656543 |
| 0.6396150164E-01 | 0.1116246419 |
| 0.6470509302E-01 | 0.1125875648 |
| 0.6545258375E-01 | 0.1135544240 |
| 0.6620397443E-01 | 0.1145252201 |
| 0.6695926562E-01 | 0.1154999539 |
| 0.6771845790E-01 | 0.1164786262 |
| 0.6848155186E-01 | 0.1174612376 |
| 0.6924854807E-01 | 0.1184477890 |
| 0.7001944714E-01 | 0.1194382811 |
| 0.7079424964E-01 | 0.1204327147 |
| 0.7157295617E-01 | 0.1214310906 |
| 0.7235556733E-01 | 0.1224334095 |
| 0.7314208372E-01 | 0.1234396722 |
| 0.7393250594E-01 | 0.1244463487 |
| 0.7472683460E-01 | 0.1254534120 |
| 0.7552507031E-01 | 0.1264608688 |
| 0.7632721368E-01 | 0.1274687131 |
| 0.7713326532E-01 | 0.1284769574 |
| 0.7794322585E-01 | 0.1294855841 |
| 0.7875709590E-01 | 0.1304945955 |
| 0.7957487609E-01 | 0.1315039593 |
| 0.8039656705E-01 | 0.1325137623 |
| 0.8122216941E-01 | 0.1335239126 |
| 0.8205168379E-01 | 0.1345344376 |
| 0.8288511085E-01 | 0.1355453348 |
| 0.8372245122E-01 | 0.1365566017 |
| 0.8456370554E-01 | 0.1375682359 |
| 0.8540887446E-01 | 0.1385802350 |

0.1395925966
0.1406053185
0.1416183982
0.1426318335
0.1436456221
0.1446597617
0.1456742501
0.1466890851
0.1477042645
0.1487197860
0.1497356477
0.1507518472
0.1517683826
0.1527852516
0.1538024524
0.1548199827
0.1558378405
0.1568560240
0.1578745309
0.1588933594
0.1599125075
0.1609319733
0.1619517548
0.1629718502
0.1639922574
0.1650129748
0.1660371510
0.1670647825
0.1680958720
0.1691304201
0.1701684274
0.1712098946
0.1722548223
0.1733032110
0.1743550614
0.1754103742
0.1764691499
0.1775313892
0.1785970926
0.1796662610
0.1807388948
0.1818149947
0.1828945613
0.1839775954
0.1850640975
0.1861540683
0.1872475084
0.1883444185
0.1894447992
0.1905486512
0.1916559751
0.1927667717
0.1938810415
0.1949987852
0.1961200035
0.1972446971

0.1983728666
0.1995045127
0.2006396361
0.2017782374
0.2029203174
0.2040658766
0.2052149159
0.2063674358
0.2075234371
0.2086829204
0.2098458865
0.2110123360
0.2121822696
0.2133556881
0.2145325921
0.2157129824
0.2168968595
0.2180842244
0.2192750775
0.2204694198
0.2216672518
0.2228685743
0.2240733880
0.2252816937
0.2264934920
0.2277087837
0.2289275695
0.2301498501
0.2313756263
0.2326048988
0.2338376684
0.2350739357
0.2363137015
0.2375569666
0.2388037317
0.2400539976
0.2413077649
0.2425650345
0.2438258071
0.2450900835
0.2463578644
0.2476291505
0.2489039427
0.2501822419
0.2514640493
0.2527493633
0.2540381873
0.2553305213
0.2566263659
0.2579257220
0.2592285903
0.2605349716
0.2618448667
0.2631582763
0.2644752014
0.2657956426

| | |
|---|---|
| 0.2671196008 | 0.3468998981 |
| 0.2684470768 | 0.3484257117 |
| 0.2697780713 | 0.3499550924 |
| 0.2711125851 | 0.3514880410 |
| 0.2724506191 | 0.3530245585 |
| 0.2737921741 | 0.3545646458 |
| 0.2751372509 | 0.3561083039 |
| 0.2764858503 | 0.3576555337 |
| 0.2778379730 | 0.3592063362 |
| 0.2791936200 | 0.3607607122 |
| 0.2805527920 | 0.3623186629 |
| 0.2819154899 | 0.3638801890 |
| 0.2832817144 | 0.3654452915 |
| 0.2846514664 | 0.3670139715 |
| 0.2860247468 | 0.3685862298 |
| 0.2874015563 | 0.3701620675 |
| 0.2887818958 | 0.3717414855 |
| 0.2901657662 | 0.3733244847 |
| 0.2915531682 | 0.3749110662 |
| 0.2929441026 | 0.3765012309 |
| 0.2943385705 | 0.3780949797 |
| 0.2957365725 | 0.3796923137 |
| 0.2971381095 | 0.3812932339 |
| 0.2985431824 | 0.3828977411 |
| 0.2999517920 | 0.3845058365 |
| 0.3013639392 | 0.3861175209 |
| 0.3027796248 | 0.3877327954 |
| 0.3041988497 | 0.3893516610 |
| 0.3056216148 | 0.3909741187 |
| 0.3070479209 | 0.3926001693 |
| 0.3084777688 | 0.3942298141 |
| 0.3099111595 | 0.3958630539 |
| 0.3113480937 | 0.3974998897 |
| 0.3127885725 | 0.3991403226 |
| 0.3142325966 | 0.4007843536 |
| 0.3156801669 | 0.4024319836 |
| 0.3171312844 | 0.4040832138 |
| 0.3185859498 | 0.4057380450 |
| 0.3200441641 | 0.4073964784 |
| 0.3215059281 | 0.4090585149 |
| 0.3229712428 | 0.4107241556 |
| 0.3244401090 | 0.4123934015 |
| 0.3259125276 | 0.4140662536 |
| 0.3273884996 | 0.4157427130 |
| 0.3288680258 | 0.4174227806 |
| 0.3303511070 | 0.4191064576 |
| 0.3318377443 | 0.4207937449 |
| 0.3333279385 | 0.4224846436 |
| 0.3348216906 | 0.4241791548 |
| 0.3363190013 | 0.4258772795 |
| 0.3378198717 | 0.4275790187 |
| 0.3393243027 | 0.4292843735 |
| 0.3408322952 | 0.4309933449 |
| 0.3423438500 | 0.4327059340 |
| 0.3438589682 | 0.4344221419 |
| 0.3453776505 | 0.4361419696 |

| | |
|---|---|
| 0.4378654182 | 0.5401914252 |
| 0.4395924887 | 0.5421231044 |
| 0.4413231823 | 0.5440584706 |
| 0.4430574999 | 0.5459975249 |
| 0.4447954426 | 0.5479402686 |
| 0.4465370116 | 0.5498867028 |
| 0.4482822080 | 0.5518368290 |
| 0.4500310327 | 0.5537906481 |
| 0.4517834868 | 0.5557481616 |
| 0.4535395716 | 0.5577093705 |
| 0.4552992880 | 0.5596742762 |
| 0.4570626371 | 0.5616428799 |
| 0.4588296200 | 0.5636151829 |
| 0.4606002379 | 0.5655911863 |
| 0.4623744918 | 0.5675708914 |
| 0.4641523829 | 0.5695542995 |
| 0.4659339122 | 0.5715414118 |
| 0.4677190808 | 0.5735322296 |
| 0.4695078898 | 0.5755267542 |
| 0.4713003405 | 0.5775249867 |
| 0.4730964338 | 0.5795269284 |
| 0.4748961709 | 0.5815325807 |
| 0.4766995529 | 0.5835419448 |
| 0.4785065809 | 0.5855550220 |
| 0.4803172561 | 0.5875718134 |
| 0.4821315795 | 0.5895923205 |
| 0.4839495524 | 0.5916165445 |
| 0.4857711758 | 0.5936444866 |
| 0.4875964510 | 0.5956761482 |
| 0.4894253789 | 0.5977115306 |
| 0.4912579608 | 0.5997506349 |
| 0.4930941977 | 0.6017934626 |
| 0.4949340910 | 0.6038400149 |
| 0.4967776416 | 0.6058902932 |
| 0.4986248507 | 0.6079442986 |
| 0.5004757195 | 0.6100020326 |
| 0.5023302493 | 0.6120634964 |
| 0.5041884413 | 0.6141286913 |
| 0.5060502965 | 0.6161976187 |
| 0.5079158151 | 0.6182702799 |
| 0.5097849998 | 0.6203466762 |
| 0.5116578512 | 0.6224268088 |
| 0.5135343705 | 0.6245106792 |
| 0.5154145587 | 0.6265982887 |
| 0.5172984171 | 0.6286896385 |
| 0.5191859470 | 0.6307847300 |
| 0.5210771493 | 0.6328835646 |
| 0.5229720254 | 0.6349861436 |
| 0.5248705764 | 0.6370924684 |
| 0.5267728036 | 0.6392025402 |
| 0.5286787080 | 0.6413163604 |
| 0.5305882909 | 0.6434339303 |
| 0.5325015536 | 0.6455552514 |
| 0.5344184971 | 0.6476803250 |
| 0.5363391228 | 0.6498091524 |
| 0.5382634317 | 0.6519417350 |

| | |
|---|---|
| 0.6540730742 | 0.7797518994 |
| 0.6562181713 | 0.7821047094 |
| 0.6583620276 | 0.7844613501 |
| 0.6605096446 | 0.7868218528 |
| 0.6626610237 | 0.7891861892 |
| 0.6648161662 | 0.7915543709 |
| 0.6669750734 | 0.7939263993 |
| 0.6691377469 | 0.7963022760 |
| 0.6713041879 | 0.7986820026 |
| 0.6734743978 | 0.8010655806 |
| 0.6756483781 | 0.8034530116 |
| 0.6778261302 | 0.8058442971 |
| 0.6800076553 | 0.8082394387 |
| 0.6821929550 | 0.8106384380 |
| 0.6843820307 | 0.8130412965 |
| 0.6865748837 | 0.8154480159 |
| 0.6887715154 | 0.8178585976 |
| 0.6909719273 | 0.8202730433 |
| 0.6931761208 | 0.8226913546 |
| 0.6953840973 | 0.8251135330 |
| 0.6975958582 | 0.8275395802 |
| 0.6998114049 | 0.8299694977 |
| 0.7020307389 | 0.8324032871 |
| 0.7042538616 | 0.8348409500 |
| 0.7064807744 | 0.8372824880 |
| 0.7087114788 | 0.8397279028 |
| 0.7109459762 | 0.8421771959 |
| 0.7131842681 | 0.8446303689 |
| 0.7154263558 | 0.8470874235 |
| 0.7176722409 | 0.8495483611 |
| 0.7199219248 | 0.8520131835 |
| 0.7221754089 | 0.8544818922 |
| 0.7244326946 | 0.8569544889 |
| 0.7266937836 | 0.8594309768 |
| 0.7289586772 | 0.8619113548 |
| 0.7312273768 | 0.8643956259 |
| 0.7334998840 | 0.8668837915 |
| 0.7357762002 | 0.8693758533 |
| 0.7380563269 | 0.8718718130 |
| 0.7403402655 | 0.8743716723 |
| 0.7426280177 | 0.8768754327 |
| 0.7449195847 | 0.8793830960 |
| 0.7472149682 | 0.8818946638 |
| 0.7495141695 | 0.8844101377 |
| 0.7518171903 | 0.8869295195 |
| 0.7541240319 | 0.8894528108 |
| 0.7564346960 | 0.8919800132 |
| 0.7587491839 | 0.8945111285 |
| 0.7610674972 | 0.8970461583 |
| 0.7633896375 | 0.8995851043 |
| 0.7657156061 | 0.9021279681 |
| 0.7680454047 | 0.9046747516 |
| 0.7703790346 | 0.9072254563 |
| 0.7727164976 | 0.9097800840 |
| 0.7750577950 | 0.9123386364 |
| 0.7774029285 | 0.9149011151 |

| | |
|---|---|
| 0.9174675219 | 1.020639816 |
| 0.9200378584 | 1.023364781 |
| 0.9226121264 | 1.026093747 |
| 0.9251903277 | 1.028826715 |
| 0.9277724638 | 1.031563688 |
| 0.9303585366 | 1.034304668 |
| 0.9329485477 | 1.037049655 |
| 0.9355424990 | 1.039798653 |
| 0.9381403920 | 1.042551663 |
| 0.9407422286 | 1.045308686 |
| 0.9433480105 | 1.048069725 |
| 0.9459577394 | 1.050834782 |
| 0.9485714171 | 1.053603858 |
| 0.9511890454 | 1.056376955 |
| 0.9538106258 | 1.059154076 |
| 0.9564361604 | 1.061935221 |
| 0.9590656507 | 1.064720394 |
| 0.9616990985 | 1.067509595 |
| 0.9643365057 | 1.070302827 |
| 0.9669778739 | 1.073100092 |
| 0.9696232050 | 1.075901392 |
| 0.9722725007 | 1.078706727 |
| 0.9749257628 | 1.081516102 |
| 0.9775829931 | 1.084329516 |
| 0.9802441933 | 1.087146973 |
| 0.9829093653 | 1.089968474 |
| 0.9855785108 | 1.092794021 |
| 0.9882516317 | 1.095623616 |
| 0.9909287297 | 1.098457261 |
| 0.9936099066 | 1.101294958 |
| 0.9962943643 | 1.104136708 |
| 0.9989839045 | 1.106982515 |
| 1.001676929 | 1.109832379 |
| 1.004373940 | 1.112686302 |
| 1.007074939 | 1.115544288 |
| 1.009779927 | 1.118406337 |
| 1.012488907 | 1.121272451 |
| 1.015201881 | 1.124142633 |
| 1.017918850 | |

Other and further uses and advantages of the multifocal IOLs according to the present invention will be more fully appreciated by those skilled in the art by reference to the specification, drawings and the appended claims.

What is claimed is:

1. A multifocal intraocular lens which comprises a lens body having at least five optical zones, a first zone comprising a central constant power zone for distance vision, a second zone comprising an annular aspheric zone, a third zone comprising a constant power zone for near vision, a fourth zone comprising an aspheric zone to bring the power back to the distance vision level and a fifth zone comprising a constant power zone for distance vision, whereby the radii for each optical zone is determined to minimize spherical aberrations and wherein the percent optical area for near and distance vision is calculated based on pupillary diameter and variation of pupillary apertures in humans for whom said lenses are designed.

2. A multifocal intraocular lens according to claim 1 which is centrosymmentric.

3. A multifocal intraocular lens according to claim 1 having five zones.

4. A multifocal intraocular lens according to claim 1 having two loops secured to the lens body, said loops being substantially symmetrically disposed.

5. A multifocal intraocular lens according to claim 1 having two loops integral with the lens body said loops being substantially symmetrically disposed.

6. A multifocal intraocular lens according to claim 1 wherein a human having a lens implanted perceives objects at an intermediate distance through 5 to 13 percent of the overall image intensity thereby enhancing the depth of field perception, objects at a near distance through 18 to 58 percent image intensity and objects at a distance through 35 to 78 percent of the image intensity.

7. A method of providing vision to a human who has had his natural lens removed which comprises implanting in the eye of the human in need thereof a multifocal intraocular lens according to claim 1.

8. A method of providing vision to a human who has had his natural lens removed which comprises implanting in the eye of the human in need thereof a multifocal intraocular lens according to claim 2.

9. A method of providing vision to a human who has had his natural lens removed which comprises implanting in the eye of the human in need thereof a multifocal intraocular lens according to claim 3.

10. A method of providing vision to a human who has had his natural lens removed which comprises implanting in the eye of the human in need thereof a multifocal intraocular lens according to claim 4.

11. A method of providing vision to a human who has had his natural lens removed which comprises implanting in the eye of the human in need thereof a multifocal intraocular lens according to claim 5.

12. A method of providing vision to a human who has had his natural lens removed which comprises implanting in the eye of the human in need thereof a multifocal intraocular lens according to claim 6.

* * * * *